(12) United States Patent
Jain et al.

(10) Patent No.: US 8,277,829 B2
(45) Date of Patent: Oct. 2, 2012

(54) NANO/MACROPOROUS BONE TISSUE SCAFFOLDS FOR REGENERATIVE MEDICINE

(75) Inventors: Himanshu Jain, Bethlehem, PA (US); Ana C. Marques, Portela (PT); Rui M. Almeida, Lisbon (PT)

(73) Assignee: Lehigh University, Bethlehem, PA (US)

( * ) Notice: Subject to any disclaimer, the term of this patent is extended or adjusted under 35 U.S.C. 154(b) by 712 days.

(21) Appl. No.: 12/377,699

(22) PCT Filed: Aug. 30, 2007

(86) PCT No.: PCT/US2007/077238
§ 371 (c)(1),
(2), (4) Date: Feb. 17, 2009

(87) PCT Pub. No.: WO2008/028036
PCT Pub. Date: Mar. 6, 2008

(65) Prior Publication Data
US 2010/0272826 A1    Oct. 28, 2010

Related U.S. Application Data

(60) Provisional application No. 60/824,161, filed on Aug. 31, 2006.

(51) Int. Cl.
*A61K 9/00* (2006.01)
*A61K 33/00* (2006.01)
*A61K 33/06* (2006.01)
*A61K 33/30* (2006.01)
*A61K 33/42* (2006.01)

(52) U.S. Cl. ........ 424/422; 424/601; 424/602; 424/641; 424/682; 424/718; 424/724

(58) Field of Classification Search .................. None
See application file for complete search history.

(56) References Cited

U.S. PATENT DOCUMENTS

| | | | |
|---|---|---|---|
| 5,009,688 | A | 4/1991 | Nakanishi |
| 6,207,098 | B1 * | 3/2001 | Nakanishi et al. ............ 264/414 |
| 6,562,744 | B1 | 5/2003 | Nakanishi et al. |
| 6,592,764 | B1 | 7/2003 | Stucky et al. |
| 6,696,258 | B1 | 2/2004 | Wei et al. |
| 6,911,192 | B2 | 6/2005 | Nakanishi |

FOREIGN PATENT DOCUMENTS

WO  WO 2007144662 A1 * 12/2007

OTHER PUBLICATIONS

Herrick et al., "Porosity?! What are we talking about, anyway?" (2002), pp. 1-12.*
Sato, Y. et al., Colloids and Surfaces A: Physiochemical and Engineering Aspects, Aug. 2001, vol. 187-188, pp. 117-122.
Jones, J. R. et al., Journal of Biomedical Materials Research. Part B, Applied Biomaterials, Jan. 15, 2004, vol. 68, No. 1, pp. 36-44.
Domingues, R. Z. et al., Journal of Biomedical Materials Research, Jan. 15, 2001, vol. 55, No. 4, pp. 468-474.
Nakanishi, K., Journal of Porous Materials, Jun. 1997, vol. 4, No. 2, pp. 67-112.
International Search Report from International Application No. PCT/US2007/077238 completed on Jan. 3, 2008.
Jones, J. R. et al., Philosophical Transactions of The Royal Society Part A, Dec. 2, 2005, vol. 364, pp. 263-281.
Saravanapavan, P. et al., Journal of Biomedical Materials Research Part A, Dec. 13, 2000, vol. 54, No. 4, pp. 608-618.

* cited by examiner

*Primary Examiner* — Sue Liu
*Assistant Examiner* — Frank Choi
(74) *Attorney, Agent, or Firm* — Rhoads & Sinon LLP; Kurt L. Ehresman

(57) ABSTRACT

A biocompatible inorganic porous material having a three-dimensional coexistent network of interconnected macropores and nanopores produced by the steps of mixing an organic water-soluble polymer (e.g., polyethylene oxide or a block copolymer of ethylene oxide and propylene oxide), an alkoxysilane, and an inorganic water-soluble calcium salt in an aqueous acid solution, such that a sol-gel process of hydrolysis and polycondensation is initiated and thereby producing a gel; drying the gel to remove solvent by evaporation; and heating the gel to remove the polymer by thermal decomposition, thereby forming an inorganic porous material, which may be suitable for use as a bone tissue scaffold.

23 Claims, 3 Drawing Sheets

NANO/MACROPOROUS BONE TISSUE SCAFFOLDS FOR REGENERATIVE MEDICINE

CROSS REFERENCE TO RELATED APPLICATIONS

This application claims the priority of U.S. provisional patent application No. 60/824,161, filed on Aug. 31, 2006, which is incorporated herein by reference in its entirety.

STATEMENT REGARDING FEDERALLY SPONSORED RESEARCH OR DEVELOPMENT

This invention was developed with financial support from the National Science Foundation (Contract No. DMR-0409588), and the United States government may have certain rights to the invention.

FIELD

This disclosure pertains to biocompatible inorganic nano/macroporous materials for use, e.g., as bone tissue scaffolds for use in regenerative medicine.

BACKGROUND

One of the great challenges of the 21$^{st}$ Century is increasing life expectancy, while at the same time maintaining quality of life in an ageing population. Regenerative medicine is, therefore, a new strategy that seeks to repair damaged or diseased tissues to their original state or function by helping natural healing processes to work faster, or by using special materials with human cell cultures, the so-called "scaffolds," which act as three-dimensional templates for cell growth and differentiation and formation of living tissues.

Synthetic scaffolds have been proposed as a new means of tissue reconstruction and repair. Scaffolds belong to a new generation of biomedical structures, which rely on the concept of regeneration of diseased or damaged tissue to its original state or function, instead of the current clinical procedures, which are based on replacement by implantation or transplantation. The latter two possess well-known drawbacks such as limited lifespan, lack of ability to self-repair, limited vascularisation of implants, limited number of donors, and possibility of rejection of transplants.

The scaffold serves as both physical support and adhesive substrate for isolated cells during in vitro culturing and subsequent in vivo implantation. Scaffolds may be used to deliver cells to desired sites in the body, to define a potential space for engineered tissue, or to guide the process of tissue development. Cell transplantation on scaffolds has been explored for the regeneration of skin, nerve, liver, and pancreas using various biological and synthetic materials. In particular, scaffolds containing dual porosity at the nano- and macroscale have been alleged to exhibit better performance in terms of crystallization of hydroxycarbonate apatite, cell adhesion and proliferation, and vascularization. Such materials, however, typically either lack sufficient mechanical strength to be of practical use or they lack an interconnected pore morphology that is compatible with vascularization.

Intended advantages of the biocompatible inorganic porous materials and methods disclosed herein satisfy one or more needs or provide other advantageous features. Other features and advantages will be made apparent from the present specification, the teachings of which extend to those embodiments that fall within the scope of the claims, regardless of whether they accomplish one or more of the aforementioned needs.

SUMMARY

Provided herein is a method, based on sol-gel processing and polymerization-induced phase separation, for preparing a silica-based bioactive scaffold. The sol-gel process is an inexpensive and versatile method for preparing scaffolds. The phase separation that occurs in the methods described herein results in an interconnected, coral-like morphology, which leads to structurally stronger materials than is achieved by other methods.

Further provided herein are biocompatible inorganic porous materials having a three-dimensional coexistent network of interconnected macropores and nanopores produced by the steps of (1) mixing an organic water-soluble polymer (e.g., polyethylene oxide or a block copolymer of ethylene oxide and propylene oxide), an alkoxysilane, and an inorganic water-soluble calcium salt in an aqueous acid solution, such that a sol-gel process of hydrolysis and polycondensation is initiated and thereby producing a gel; (2) drying the gel to remove solvent by evaporation; and (3) heating the gel to remove the polymer by thermal decomposition, thereby forming an inorganic porous material, which may be suitable for use as a bone tissue scaffold.

The methods and materials described herein provide a novel and simple procedure for the preparation of silica-based bioactive porous bone tissue scaffold, in which the pore structure, having interconnected pores of both hundreds of micrometers and several to tens of nanometers in size, is formulated for enhanced bone regeneration performance. Unlike existing sol-gel materials, which are inherently nanoporous, the silica-based bone tissue scaffolds are made with a controlled nano/macroporosity, which enhances bone regeneration performance.

Such scaffolds may be used in tissue engineering and regeneration techniques, as well as stimulating cell growth and differentiation, as well as the formation of tissues. This process may include the harvesting and culture of stem cells from the patient on the scaffold in vitro, thereby creating a tissue/scaffold biocomposite that is then implanted in the damaged site, with tissue regeneration occurring at the rate at which the scaffold resorbs.

The synthetic methods described herein allow for the preparation of bone tissue scaffolds with a controlled nano/macroporosity, which includes interconnected macropores above the minimum pore size required for tissue in-growth and eventually vascularization (e.g., approximately 100 µm in size). The interconnected, coral-like morphology results from spinodal phase separation that occurs simultaneously with gelation and leads to a pore volume of ca. 50-65%, yielding materials with mechanical properties that match those of the host bone, e.g., materials mechanically stronger than the ones achieved by other methods.

Other features and advantages will be apparent from the following more detailed description of some example embodiments.

DETAILED DESCRIPTION

Figure 1:
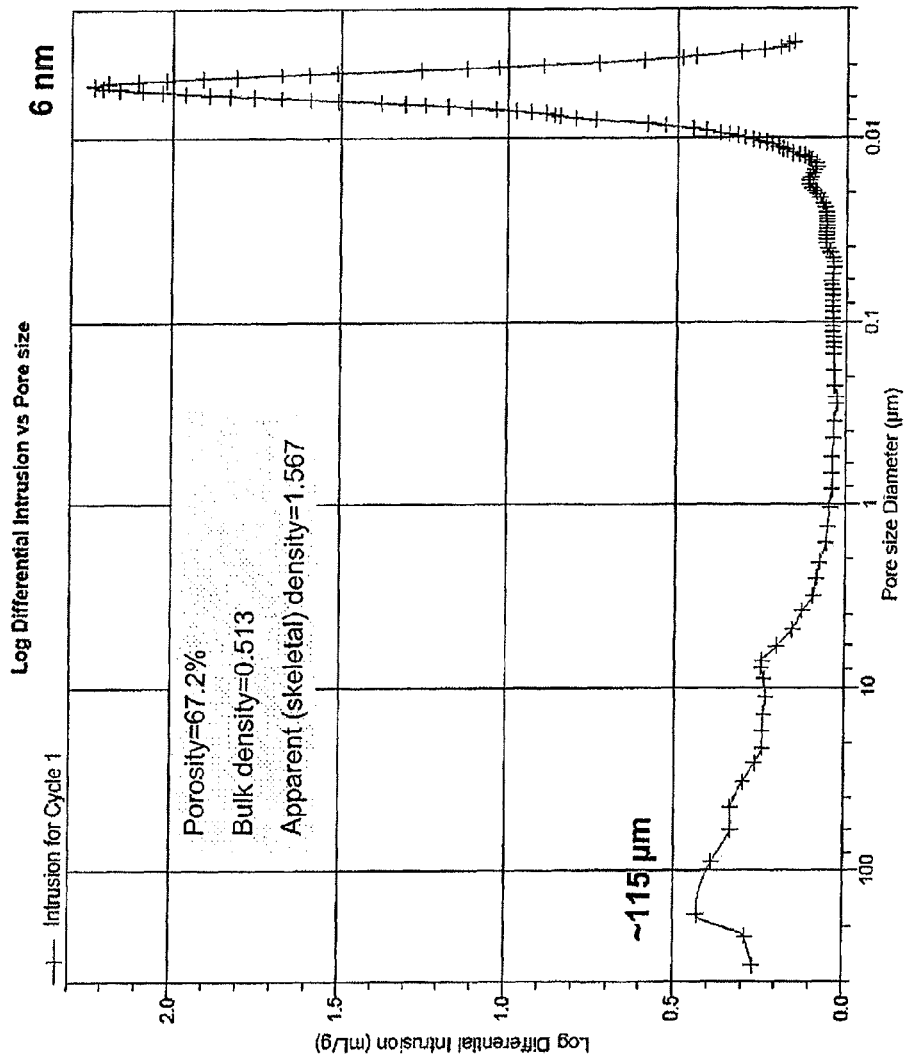
FIG. 1 depicts the bimodal distribution of pore size in a 70% $SiO_2$:30% CaO biocompatible inorganic porous bone scaffold material, in which the organic water-soluble polymer used during manufacture was a block copolymer of ethylene oxide and propylene oxide (results obtained by mercury intrusion porosimetry).

In an exemplary embodiment, a method for preparing nano/macroporous bone scaffold materials is based on the sol-gel process and polymerization-induced phase separation parallel to the sol-gel transition. For example, a solution is prepared containing a metal alkoxide and an organic, water-soluble polymer. Hydrolysis and condensation of the metal alkoxide occur with the formation of a sol (colloidal solution of polymerized molecular units), followed by gelation of the sol. Then the gel undergoes solvent exchange in basic conditions. Finally, it is dried and heat treated in order to obtain the porous material. The interconnected, coral-like morphology results from polymerization-induced (spinodal) phase separation that occurs simultaneously with the sol-gel transition and leads to a pore volume at ca. 50-65%. "Spinodal" refers to the phenomenon whereby for an arbitrarily small fluctuation in composition wherein one part of the system gets more concentrated at the expense of another, the system is inherently unstable and phase separation occurs. That is, an initially single-phase solution containing a polymerizable component becomes less stable with an increase of the molecular weight of the component, resulting in the separation into two different phases. Polymerization and gel-forming reaction are therefore the cause for phase separation.

The presence of organic polymers, such as polyethylene oxide ("PEO"), which tend to form strong hydrogen bonds with metal oligomers (e.g., silica), leads to the occurrence of phase separation, which yields two phases, one rich in polymer plus inorganic oxides (e.g., silica) and the other rich in solvent. When this phenomenon occurs contemporaneously with the sol-gel transition, the gelation freezes the interconnected, coral-like structure that has resulted from phase separation by spinodal decomposition. Drying of the gel then removes the solvent from the solvent-rich phase by evaporation, thereby forming interconnected macropores of about 1 μm to about 200 μm in size, while heat treatment decomposes and removes the organic polymer. The nanoporous structure (e.g., about 5 nm to about 40 nm) of such macroporous gel skeletons may be tailored by solvent exchange procedures under basic conditions (e.g., with ammonia solution), resulting in an increase of the size of the original nanopores inherent to the inorganic sol-gel process.

The formation of interconnected macropores through other prior art techniques, such as foaming of a sol using a surfactant, requires very high pore volumes (ca. 80-90%), because they are spherical. The resulting materials are structurally weak, whereas the morphology formed during spinodal phase separation leads to interconnected pores at ca. 50-65% pore volume and, therefore, to mechanically stronger materials. The sol-gel process also permits control of the factors that affect bioactivity, namely the composition (e.g., Ca/P molar ratio) and texture (pore size and shape). In addition, it is an inexpensive and versatile method for preparing pure and homogeneous oxide materials. Furthermore, the shape of the sol-gel derived materials is the same as that of the container/mould for the sol at the moment of gelation.

The nano/macroporosity presented by the bioactive materials disclosed herein is ideal for use as bone tissue scaffolds because macropores in excess of 100 μm are required for bone cell in-growth and proliferation and vascularisation, whereas nanopores (in the range of 5-50 nm) are thought to be useful for the rapid crystallization of hydroxycarbonate apatite and cell adhesion.

Further provided herein is a method for producing a biocompatible inorganic porous material having a three-dimensional coexistent network of interconnected macropores and nanopores, which method includes steps of mixing an organic water-soluble polymer, an alkoxysilane, and an inorganic water-soluble calcium salt in an aqueous acid solution, such that a sol-gel process of hydrolysis and polycondensation is initiated and thereby producing a gel; drying the gel to remove solvent by evaporation; and heating the gel to remove the polymer by thermal decomposition, thereby forming an inorganic porous material. It is believed that the drying step produces macropores, and the heating step produces nanopores. (The drying step produces most of the macropores, while the heating step produces most of the nanopores). For example, the macropores may have an average pore size of greater than about 1 micrometer and the nanopores may have an average pore size of from about 5 nanometers to about 40 nanometers.

In another embodiment, the aforementioned method includes a step of aging the gel at a temperature of about 40° C. In yet another embodiment, the drying step occurs at a temperature (e.g., using a programmable temperature program) from about 40° C. to about 80° C. (e.g., about 60° C., or even as high as 180° C.). In still another embodiment, the heating step occurs at a temperature of greater than about 600° C.

In another embodiment, a method for producing a biocompatible inorganic porous material includes a step of immersing the gel into an aqueous ammonia solution, such that solvent exchange occurs (e.g., removal of alcohols and other solvents from the gel).

A method for producing a biocompatible inorganic porous material includes the use of an alkoxysilane as a reagent, which may be tetramethoxysilane, tetraethoxysilane, methyltriethoxysilane, (3-glycidoxypropyl)trimethoxysilane, or a combination thereof. Likewise, the inorganic water-soluble calcium salt used in the method may be calcium nitrate or a hydrates thereof (e.g., $Ca(NO_3)_2 \cdot 4H_2O$).

Organic polymers are added to the sol-gel solution because they are soluble in the sol-gel solution and establish strong hydrogen bonds with the metal oligomers. They may include water-soluble polymers, such as poly(ethylene oxide) (PEO), or poly(ethylene glycol) (PEG), or amphiphilic substances, such as block copolymers (e.g., ethylene oxide-propylene oxide-ethylene oxide). Further examples include the PLURONIC® (a registered trademark of BASF Corp. of New Jersey) polymers, which are block copolymers based on ethylene oxide and propylene oxide. Polyethylene glycol ("PEG") and polyethylene oxide ("PEO") are polymers composed of repeating subunits of identical structure. Poly(ethylene glycol) or poly(ethylene oxide) refer to an oligomer or polymer of ethylene oxide. PEG differs from PEO only by its smaller molecular weight. PEG and PEO has the following structure: HO—($CH_2$—$CH_2$—O)$_n$—H. PEO undergoes thermo-oxidative and oxidative destruction at the temperature above about 300° C., and it forms complexes with alkaline earth metals (such as $Ca^{2+}$).

Accordingly, an example embodiment of a method for producing a biocompatible inorganic porous material includes the use of an organic water-soluble polymer, which may be a polymer of ethylene oxide, a polymer of propylene oxide, a polymer of ethylene glycol, a copolymer of ethylene oxide and propylene oxide, or a mixture thereof. For example, the organic water-soluble polymer may be polyethylene oxide or a block copolymer of ethylene oxide and propylene oxide.

Depending on the desired properties of the resulting material, a method for producing a biocompatible inorganic porous material may include additional reagents. For example, the aqueous acid solution may include a trialkyl orthophosphate such as triethyl orthophosphate, which acts as a phosphorous source during the polymerization reaction. In another embodiment, the aqueous acid solution may include a water-soluble zinc salt such as zinc nitrate, which acts as a zinc source during the polymerization reaction. The reaction mixture may also include a pore expander additive such as urea or 1,3,5-trimethylbenzene, which expands the size of the nanopores within the material.

A method for producing a biocompatible inorganic porous material is typically conducted in an acidic reaction solution. Accordingly, the aqueous acid solution may include an acid such as hydrofluoric acid, nitric acid, acetic acid, or a combination thereof.

In another embodiment, a biocompatible inorganic porous material having a three-dimensional coexistent network of interconnected macropores and nanopores may be produced by the steps of mixing an organic water-soluble polymer, an alkoxysilane, and an inorganic water-soluble calcium salt in an aqueous acid solution, such that a sol-gel process of hydrolysis and polycondensation is initiated and thereby producing a gel; drying the gel to remove solvent by evaporation; and heating the gel to remove the polymer by thermal decomposition, thereby forming an inorganic porous material.

An example biocompatible inorganic porous material may have a phosphorous:calcium molar ratio of from about 0.0 to about 0.3 (or even as high as 0.6). In another example, a biocompatible inorganic porous material may have a zinc:calcium molar ratio of from about 0.0 to about 0.3.

Also provided herein is a method of inducing bone growth or regeneration in a mammal comprising a step of implanting a biocompatible inorganic porous material in a mammal in need thereof, such that hydroxycarbonate apatite growth occurs on an interior or exterior surface of the biocompatible inorganic porous material. Also provided is a method of stimulating cell growth or differentiation comprising a step of placing one or more cells onto a surface of a biocompatible inorganic porous material. In an embodiment, the biocompatible inorganic porous material may be impregnated with a pharmaceutically active compound and thereby function as a drug delivery system.

Additional embodiments are further exemplified by the following examples, which should not be construed as limiting.

EXAMPLES

70% $SiO_2$:30% CaO (mol%), using poly(ethylene oxide), PEO, as the organic, water soluble polymer.

1.88 g of PEO (Alfa Aesar, molecular weight: 100,000) was dissolved in 20 mL of a 0.01 N acetic acid ($CH_3COOH$) aqueous solution. To this solution, 0.90 g of urea and 9 mL of tetramethoxysilane ("TMOS") were added while vigorously stirring. After ca. 5 min stirring, 6.18 g of calcium nitrate tetrahydrate, $Ca(NO_3)_2 \cdot 4H_2O$, were added and stirred until the calcium salt was dissolved in the solution (ca. 10 min). Six drops of hydrofluoric acid (HF, 60% v/v) were then added in order to accelerate gelation. The sol was transferred to a closed container and kept at 40° C. without stirring, until gelation occurred (gelation time was ca. 30 min). The gel was aged for 20 h at 40° C., plus 1 day at room temperature (uncovered container). Solvent exchange was then performed by immersing the wet gel in deionised water at room temperature for 3 h and then in 1 N ammonia ($NH_4OH$) aqueous solution for 1 day at 40° C. The resulting gel was dried at temperatures in the range of 40° C. to 180° C. (ramp profile) for 3 days, and heat treated sequentially at 600° C. (1 h) and 700° C. (2 h), with heating and cooling (to room temperature) rates of 100° C./h.

77% $SiO_2$:19% CaO:4% $P_2O_5$ (mol%), using a triblock copolymer (ethylene oxide-propylene oxide-ethylene oxide), $(EO)_{20}$-$(PO)_{70}$-$(EO)_{20}$, also known as Pluronic P123.

10.6 mL of tetramethoxysilane ("TMOS") was added to 10.6 mL of a 2 N nitric acid ($HNO_3$) aqueous solution. The solution was stirred until room temperature was reached. To this solution, 0.70 ml of triethyl orthophosphate ("TEP") were added at room temperature, followed by stirring for ca. 15 min. Then, 4.62 g of calcium nitrate tetrahydrate, $Ca(NO_3)_2 \cdot 4H_2O$ was added and stirring was performed until the calcium salt was dissolved in the solution (ca. 10 min). Next, a previously prepared solution containing 4.20 g of Pluronic P123 (Sigma-Aldrich, molecular weight: 5800), 1 mL of 1,3,5-trimethylbenzene ("TMB") and 12 mL of deionised water were added at 0° C. while vigorously stirring. Six drops of HF were then added in order to accelerate gelation. The sol was transferred to a closed container and kept at 40° C. without stirring until gelation occurred (gelation time was ca. 10 min). The gel was aged for 20 h at 40° C., plus 1 day at room temperature (uncovered container). Solvent exchange was then performed by immersing the wet gel in deionised water at room temperature for 3 h and then in a 1 N ammonia ($NH_4OH$) aqueous solution for 1 day at 40° C. The resulting gel was dried at 60° C. for 2 days, and heat treated sequentially at 600° C. (1 h) and 700° C. (4 h), with heating and cooling (to room temperature) rates of 100° C./h.

Figure 2:
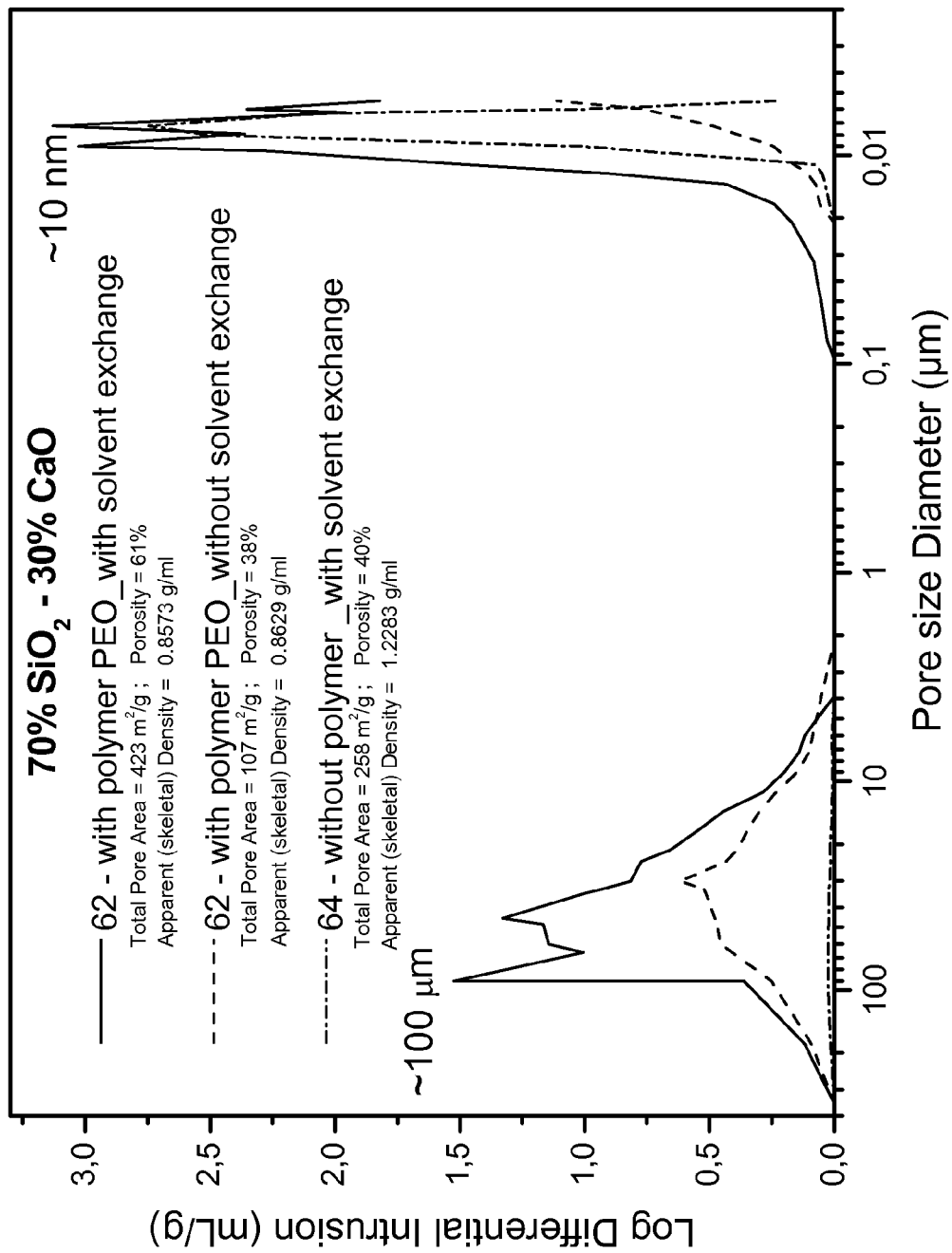
FIG. 2 depicts the bimodal distribution of pore size in a 70% $SiO_2$:30% CaO biocompatible inorganic porous bone scaffold material, prepared with and without an organic water soluble polymer (PEO) and with and without solvent exchange procedures (results obtained from mercury intrusion porosimetry).
Figure 3:
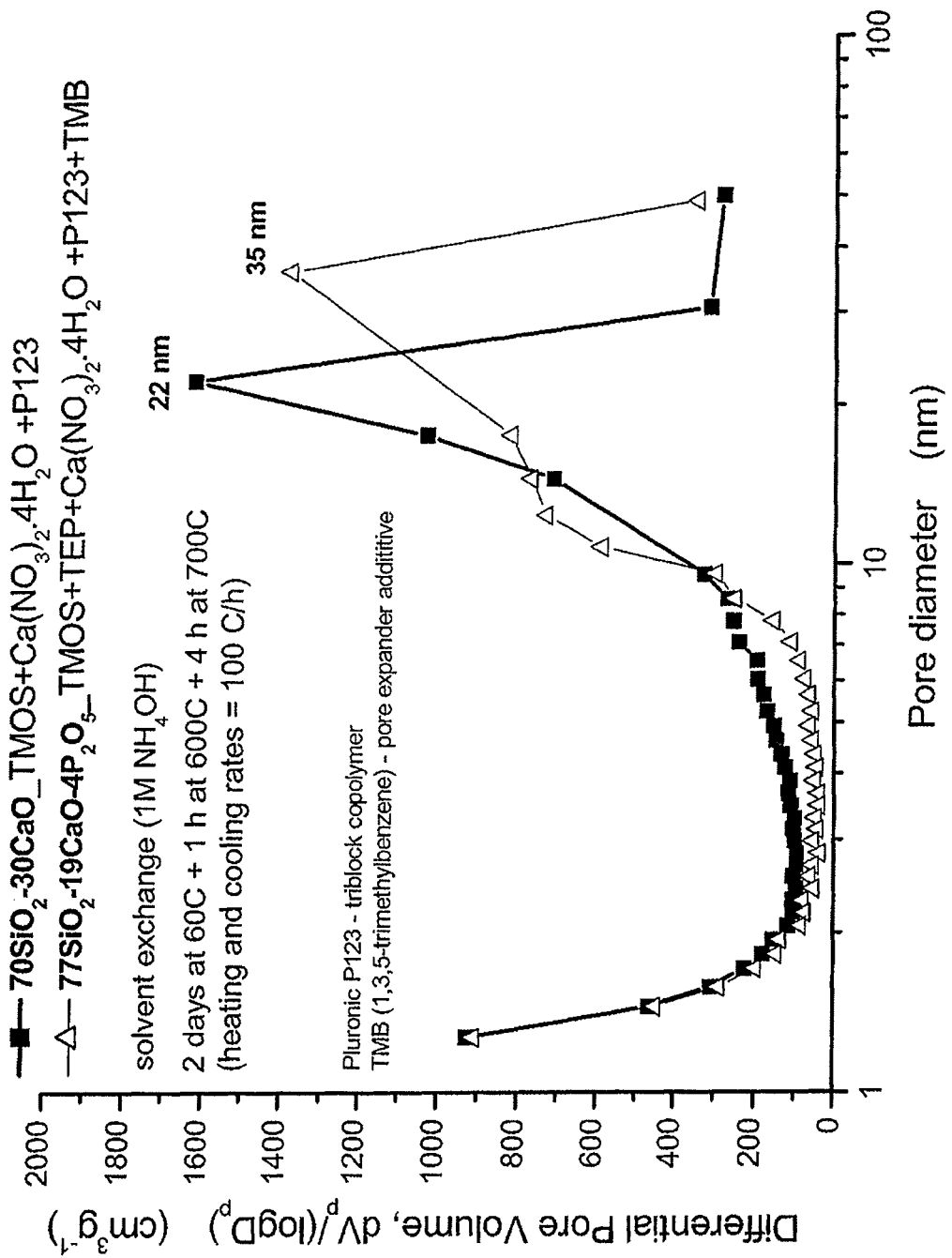
FIG. 3 depicts pore size distribution in a 70% $SiO_2$:30% CaO biocompatible inorganic porous bone scaffold material, as well as a 77% $SiO_2$:19% CaO:4% $P_2O_5$ biocompatible inorganic porous bone scaffold material, in which the organic water-soluble polymer used during manufacture was a block copolymer of ethylene oxide and propylene oxide, and in which 1,3,5-trimethylbenzene was used as a pore expander additive (results obtained from nitrogen adsorption).

Referring to the Drawings, FIG. 1 illustrates the porosimetry results from a biocompatible inorganic porous material made from TMOS, $Ca(NO_3)_2 \cdot 4H_2O$, and Pluronic P123. A bimodal distribution is clearly visible, with macropores having an average pore size of about 115 μm and nanopores having an average pore size of about 6 nm. The effect of organic polymer (PEO) addition and solvent exchange procedure is illustrated in FIG. 2, in which the sample without organic polymer does not present macropores and the sample without solvent exchange presents smaller nanopores. FIG. 3 shows the effect of composition on nanopore size, when Pluronic P123 is used as the organic polymer. For all of the materials described in FIGS. 1-3, each of which have a bimodal pore size distribution, electron microscopy clearly showed an interconnected network of macropores and nanopores, which were consistent with the pore sizes determined by porosimetry.

Although only a few embodiments have been described in detail in this disclosure, those skilled in the art who review this disclosure will readily appreciate that many modifications are possible (e.g., variations in reagents, solvents, reaction times, additives, values of parameters, etc.) without materially departing from the novel teachings and advantages of the subject matter hereof. Accordingly, all such modifications are intended to be included within the scope of the present application. Furthermore, the order or sequence of any process or method steps may be varied according to alternative embodiments. Other substitutions, modifications, changes and omissions may be made in the design, operating conditions and arrangement of the exemplary embodiments without departing from the scope of the present application.

The invention claimed is:

1. A method for producing a biocompatible inorganic porous material having a three-dimensional network of coexistent interconnected macropores and nanopores, which method comprises steps of:
mixing an organic water-soluble polymer, an alkoxysilane, and an inorganic water-soluble calcium salt in an aqueous acid solution, such that a sol-gel process of hydrolysis and polycondensation is initiated and thereby producing a gel;
drying said gel to remove solvent by evaporation; and
heating said gel to remove said polymer by thermal decomposition, thereby forming an inorganic porous bioactive material, that is characterized by interconnected multimodal porosity including nanopores of about 5 to about 40 nm in size, macropores from about 1 μm to about 300 μm in size, corresponding to a volume fraction of porosity between about 38 to about 67 percent, as determined by a porisimetry method selected from the group consisting of mercury intrusion porisimetry and nitrogen adsorption porisimetry.

2. The method according to claim 1, wherein said drying step produces the nanopores, and said heating step produces the macropores.

3. The method according to claim 2, wherein the step of mixing is performed without foaming.

4. The method according to claim 1, further comprising a step of aging said gel at a temperature of about 40° C.

5. The method according to claim 1, wherein said drying step occurs at a temperature of from about 40° C. to about 180° C.

6. The method according to claim 1, wherein said heating step occurs at a temperature of greater than about 600° C.

7. The method according to claim 1, further comprising a step of immersing said gel into an aqueous ammonia solution, such that solvent exchange occurs.

8. The method according to claim 1, wherein said alkoxysilane is selected from the group consisting of tetramethoxysilane, tetraethoxysilane, methyltriethoxysilane, (3-glycidoxypropyl)trimethoxysilane, and combinations thereof.

9. The method according to claim 1, wherein said inorganic water-soluble calcium salt is selected from the group consisting of calcium nitrate and hydrates thereof.

10. The method according to claim 1, wherein said organic water-soluble polymer is selected from the group consisting of polymers of ethylene oxide, polymers of propylene oxide, polymers of ethylene glycol, copolymers of ethylene oxide and propylene oxide, and mixtures thereof.

11. The method according to claim 1, wherein said organic water-soluble polymer is polyethylene oxide or a block copolymer of ethylene oxide and propylene oxide.

12. The method according to claim 1, wherein said aqueous acid solution further comprises a trialkyl orthophosphate.

13. The method according to claim 12, wherein said trialkyl orthophosphate is triethyl orthophosphate.

14. The method according to claim 1, wherein said aqueous acid solution further comprises a water-soluble zinc salt.

15. The method according to claim 14, wherein said water-soluble zinc salt is zinc nitrate.

16. The method according to claim 1, wherein said aqueous acid solution further comprises a pore expander additive.

17. The method according to claim 16, wherein said pore expander additive is urea or 1,3,5-trimethylbenzene.

18. The method according to claim 1, wherein said aqueous acid solution comprises an acid selected from the group consisting of hydrofluoric acid, nitric acid, acetic acid, and combinations thereof.

19. A biocompatible inorganic porous material having a three-dimensional network of coexistent interconnected macropores and nanopores produced by the steps of:
mixing an organic water-soluble polymer, an alkoxysilane, and an inorganic water-Soluble calcium salt in an aqueous acid solution, such that a sol-gel process of hydrolysis and polycondensation is initiated and thereby producing a gel;
drying said gel to remove solvent by evaporation; and
heating said gel to remove said polymer by thermal decomposition, thereby forming an inorganic porous bioactive material, wherein the material is characterized by interconnected multimodal porosity including nanopores of about 5 to about 40 nm in size, macropores from about 1 μm to about 300 μm in size, corresponding to a volume fraction of porosity between about 38 to about 67 percent, as determined by a porisimetry method selected from the group consisting of mercury intrusion porisimetry and nitrogen adsorption porisimetry.

20. The material according to claim 19, wherein said inorganic porous material has a phosphorous:calcium molar ratio of from about 0.0 to about 0.6.

21. The material according to claim 19, wherein said inorganic porous material has a zinc:calcium molar ratio of from about 0.0 to about 0.3.

22. A method of inducing bone growth or regeneration in a mammal comprising a step of implanting a biocompatible inorganic porous material according to claim 19 in a mammal in need thereof, such that hydroxycarbonate apatite growth occurs on an interior or exterior surface of said biocompatible inorganic porous material.

23. A method of stimulating cell growth or differentiation comprising a step of placing one or more cells onto a surface of a biocompatible inorganic porous material according to claim 19.

* * * * *

UNITED STATES PATENT AND TRADEMARK OFFICE
CERTIFICATE OF CORRECTION

PATENT NO. : 8,277,829 B2
APPLICATION NO. : 12/377699
DATED : October 2, 2012
INVENTOR(S) : Himanshu Jain, Ana C. Marques and Rui M. Almeida It is certified that error appears in the above-identified patent and that said Letters Patent is hereby corrected as shown below:

In the Specification

In the Description:
Column 1, Lines 16-19, change "This invention was developed with financial support from the National Science Foundation (Contract No. DMR-0409588), and the United States government may have certain rights to the invention." to "This invention was made with government support under DMR0409588 awarded by the National Science Foundation. The government has certain rights in the invention."

Signed and Sealed this
Second Day of August, 2022

Katherine Kelly Vidal
*Director of the United States Patent and Trademark Office*